(12) United States Patent
Balthasart et al.

(10) Patent No.: US 8,049,047 B2
(45) Date of Patent: Nov. 1, 2011

(54) PROCESS FOR THE MANUFACTURE OF 1,2-DICHLOROETHANE

(75) Inventors: Dominique Balthasart, Brussels (BE); Michel Lempereur, Corbais (BE); Michel Strebelle, Brussels (BE)

(73) Assignee: Solvay (Societé Anonyme), Brussels (BE)

( * ) Notice: Subject to any disclaimer, the term of this patent is extended or adjusted under 35 U.S.C. 154(b) by 12 days.

(21) Appl. No.: 12/304,297

(22) PCT Filed: Jun. 21, 2007

(86) PCT No.: PCT/EP2007/056187
§ 371 (c)(1),
(2), (4) Date: Dec. 11, 2008

(87) PCT Pub. No.: WO2007/147870
PCT Pub. Date: Dec. 27, 2007

(65) Prior Publication Data
US 2009/0326179 A1    Dec. 31, 2009

(30) Foreign Application Priority Data
Jun. 23, 2006 (FR) ..................... 06.05625

(51) Int. Cl.
*C08F 14/06* (2006.01)
*C07C 17/00* (2006.01)
*C07C 19/01* (2006.01)
(52) U.S. Cl. ........................ 570/181; 526/344
(58) Field of Classification Search ............ 526/344
See application file for complete search history.

(56) References Cited

U.S. PATENT DOCUMENTS

| | | |
|---|---|---|
| 4,910,354 A | 3/1990 | Derleth et al. |
| 5,260,247 A | 11/1993 | Helmut et al. |
| 5,527,754 A | 6/1996 | Derleth et al. |
| 5,789,499 A | 8/1998 | Masuko et al. |
| 6,803,342 B1 | 10/2004 | Derleth et al. |
| 7,667,084 B2 | 2/2010 | Strebelle et al. |
| 2004/0267063 A1 | 12/2004 | Harth et al. |
| 2008/0108856 A1 | 5/2008 | Strebelle et al. |
| 2008/0207965 A1* | 8/2008 | Strebelle et al. ............... 570/225 |
| 2008/0207966 A1 | 8/2008 | Balthasart et al. |
| 2008/0207967 A1 | 8/2008 | Strebelle et al. |
| 2008/0207968 A1* | 8/2008 | Strebelle et al. ............... 570/244 |
| 2009/0203854 A1 | 8/2009 | Strebelle et al. |
| 2009/0270568 A1 | 10/2009 | Strebelle et al. |
| 2009/0270579 A1 | 10/2009 | Balthasart et al. |

FOREIGN PATENT DOCUMENTS

| | | |
|---|---|---|
| DE | 1443707 A | 11/1968 |
| EP | 0053335 A1 | 6/1982 |
| EP | 0255156 A1 | 2/1988 |
| EP | 0494474 A1 | 7/1992 |
| EP | 0657212 A1 | 6/1995 |
| EP | 0657213 A1 | 6/1995 |
| EP | 0883588 B1 | 9/2001 |
| GB | 0970961 A | 9/1964 |
| GB | 1096594 A | 12/1967 |
| GB | 1207767 A | 10/1970 |
| NL | 6901398 | 11/1969 |
| WO | WO0026164 A1 | 5/2000 |
| WO | WO0138274 A1 | 5/2001 |
| WO | WO 03/044125 A2 | 5/2003 |
| WO | WO03048088 A1 | 6/2003 |
| WO | W02006/067188 A1 | 6/2006 |
| WO | W02006/067190 A1 | 6/2006 |
| WO | W02006/067191 A1 | 6/2006 |
| WO | W02006/067192 A1 | 6/2006 |
| WO | WO 2006/067193 A1 | 6/2006 |
| WO | W02008/000693 A1 | 1/2008 |
| WO | W02008/000702 A1 | 1/2008 |
| WO | W02008/000705 A1 | 1/2008 |
| WO | W02008/107468 A1 | 9/2008 |
| WO | WO 2009/106479 A1 | 9/2009 |
| WO | WO2009/147076 A1 | 12/2009 |
| WO | WO2009/147083 A1 | 12/2009 |
| WO | WO2009/147100 A1 | 12/2009 |
| WO | WO2009/147101 A1 | 12/2009 |

OTHER PUBLICATIONS

Zimmermann H. et al., "Ethylene" in Ullmann's Encyclopedia of Industrial Chemistry, Jun. 15, 2000, p. 1-47, Wiley (47 p.).
PCT International Search Report dated Sep. 14, 2007 for International Application No. PCT/EP2007/056187 (3 p.).
U.S. Appl. No. 12/919,101, filed Aug. 24, 2010, Andre Petitjean et al.
U.S. Appl. No. 12/995,486, filed Dec. 1, 2010, Lempereur et al.
U.S. Appl. No. 12/995,518, filed Dec. 1, 2010, Petitjean et al.
U.S. Appl. No. 12/995,539, filed Dec. 1, 2010, Lempereur et al.
U.S. Appl. No. 12/995,509, filed Dec. 1, 2010, Kotter et al.

* cited by examiner

*Primary Examiner* — David W Wu
*Assistant Examiner* — Sonya Wright
(74) *Attorney, Agent, or Firm* — Beatrice C. Ortego

(57) ABSTRACT

Process for the manufacture of 1,2-dichloroethane (DCE) starting with a hydrocarbon source which is subjected to a cracking thus producing a mixture of cracking products then subjected to treatment steps to obtain a mixture of products containing ethylene. The mixture is afterwards subjected to a first separation step into a fraction enriched with the compounds that are lighter than ethylene containing some of the ethylene conveyed to a chlorination reactor in which most of the ethylene is converted to DCE, and into a fraction F1 which is subjected to a second separation step into a fraction F2 and into a heavy fraction. Fraction F2 is afterwards subjected to a third separation step into a fraction enriched with ethylene conveyed to an oxychlorination reactor in which most of the ethylene is converted to DCE, and into a fraction F3 mainly composed of ethane.

20 Claims, 1 Drawing Sheet

PROCESS FOR THE MANUFACTURE OF 1,2-DICHLOROETHANE

CROSS-REFERENCE TO RELATED APPLICATIONS

Figure 1:
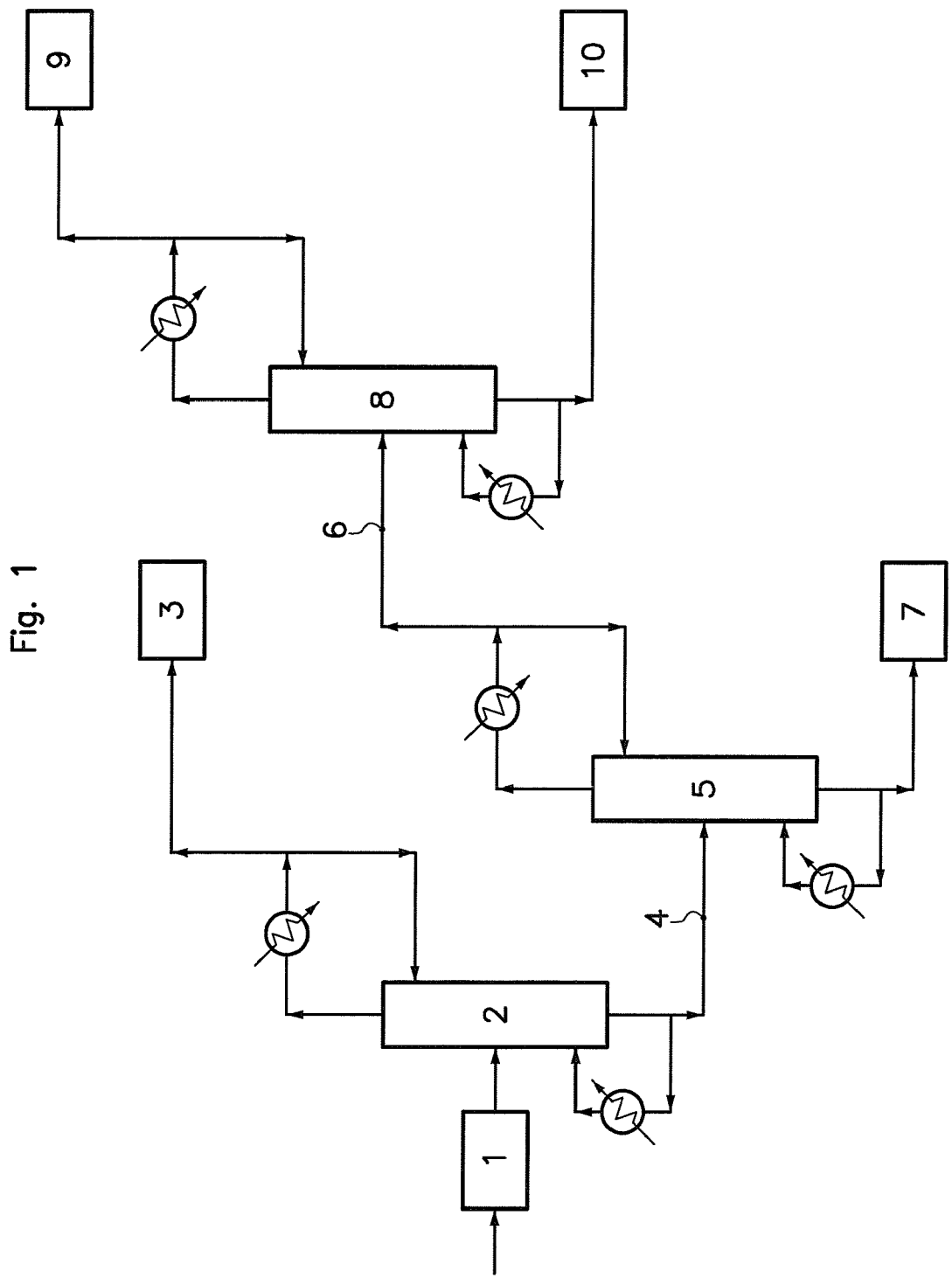

The present application is a U.S. national stage application under 35 U.S.C. §371 of International Application No. PCT/EP2007/056187, filed Jun. 21, 2007, which claims benefit of French patent applications FR 06.05625 filed on Jun. 23, 2006, all of these applications being herein incorporated by reference in their entirety for all purposes.

The present invention relates to a process for the manufacture of 1,2-dichloroethane (DCE), a process for the manufacture of vinyl chloride (VC) and a process for the manufacture of polyvinyl chloride (PVC).

To date, ethylene which is more than 99.8% pure is normally used for the manufacture of DCE. This very high purity ethylene is obtained via the cracking of various petroleum products, followed by numerous complex and expensive separation operations in order to isolate the ethylene from the other products of cracking and to obtain a product of very high purity.

Given the high cost linked to the production of ethylene of such high purity, various processes for the manufacture of DCE using ethylene having a purity of less than 99.8% have been developed. These processes have the advantage of reducing the costs by simplifying the course of separating the products resulting from the cracking and by thus abandoning complex separations which are of no benefit for the manufacture of DCE.

For example, Patent Application WO 00/26164 describes a process for the manufacture of DCE by simplified cracking of ethane coupled with chlorination of ethylene. To this effect, an ethylene chlorination step takes place in the presence of the impurities obtained during the cracking of the ethane.

Patent Application WO 03/48088 itself describes a process for the manufacture of DCE by dehydrogenation of ethane giving rise to the formation of a fraction comprising ethane, ethylene and impurities including hydrogen, which fraction is then subjected to chlorination and/or oxychlorination.

The processes described have nevertheless the disadvantage that the ethylene obtained cannot be used for an ethylene chlorination/oxychlorination process given that the ethylene contains impurities whose presence during the oxychlorination reaction could cause operating problems, namely poisoning of the catalyst by heavy products and uneconomical conversion of the hydrogen present. This hydrogen conversion would consume oxygen and release a high heat of reaction. This would then limit the capability of the oxychlorination reactor, generally linked to the heat exchange capability. An unusually high investment must therefore be expended in order to guarantee the heat exchange area, and thereby the reactor volume, caused by the presence of hydrogen in the mixture. The option taken of burning the hydrogen in a separate reactor does not resolve the difficulty because it requires a large amount of oxygen, a stoichiometric amount relative to hydrogen, and also a large surface area for exchange to eliminate this heat of combustion, consequently it has a significant ethylene consumption and it may have problems linked to safety. Finally, the removal of the water formed leads to an increase in the production costs.

One object of the present invention itself is to provide a process using ethylene having a purity of less than 99.8% which has the advantage of reducing the costs by abandoning complex separations in order to isolate the ethylene from the other products of cracking that are of no benefit for the manufacture of DCE, and which has the advantage of avoiding the abovementioned problems.

To this effect, the invention relates to a process for manufacturing DCE starting with a hydrocarbon source according to which:
a) the hydrocarbon source is subjected to a first cracking step, namely a pyrolysis step carried out in at least one cracking furnace, thus producing a mixture of cracking products;
b) said mixture of cracking products is subjected to a series of treatment steps making it possible to obtain a mixture of products containing ethylene and other constituents;
c) said mixture of products containing ethylene is subjected to a first separation step S1 which consists of separating said mixture of products inside a column C1, into a fraction enriched with the compounds that are lighter than ethylene containing some of the ethylene (fraction A) and into a fraction F1;
d) fraction F1 is subjected to a second separation step S2 which consists of separating fraction F1 inside a column C2 into a fraction F2 and into a heavy fraction (fraction C);
e) fraction F2 is subjected to a third separation step S3 which consists of separating fraction F2 inside a column C3 into a fraction enriched with ethylene (fraction B) and into a fraction F3 mainly composed of ethane;
f) fraction A is conveyed to a chlorination reactor and fraction B is conveyed to an oxychlorination reactor, reactors in which most of the ethylene present in fractions A and B is converted to 1,2-dichloroethane; and
g) the 1,2-dichloroethane obtained is separated from the streams of products derived from the chlorination and oxychlorination reactors.

The hydrocarbon source considered may be any known hydrocarbon source. Preferably, the hydrocarbon source subjected to the first cracking step (step a)) is chosen from the group consisting of naphtha, gas oil, natural gas liquid, ethane, propane, butane, isobutane and mixtures thereof. In a particularly preferred manner, the hydrocarbon source is chosen from the group consisting of ethane, propane, butane and propane/butane mixtures. In a more particularly preferred manner, the hydrocarbon source is chosen from the group consisting of propane, butane and propane/butane mixtures. The propane/butane mixtures may exist as such or may consist of mixtures of propane and butane.

The expression "ethane, propane, butane and propane/butane mixtures" is understood to mean, for the purposes of the present invention, products that are commercially available, namely that consist mainly of the pure product (ethane, propane, butane or propane/butane as a mixture) and secondarily of other saturated or unsaturated hydrocarbons, which are lighter or heavier than the pure product itself.

The expression "first cracking step", namely a pyrolysis step carried out in at least one cracking furnace (step a)), is understood to mean a conversion, under the action of heat, of the hydrocarbon source in the presence or absence of third compounds such as water, oxygen, a sulphur derivative and/or a catalyst so as to give rise to the formation of a mixture of cracking products.

This mixture of cracking products advantageously comprises hydrogen, carbon monoxide, carbon dioxide, nitrogen, oxygen, hydrogen sulphide, organic compounds comprising at least one carbon atom, and water.

Step a) is carried out in at least one cracking furnace. Step a) is preferably carried out in at least two cracking furnaces and particularly preferably in at least three cracking furnaces. Step a) is preferably carried out in at most five cracking furnaces and particularly preferably in at most four cracking furnaces. With a more particular advantage, an additional cracking furnace is available to replace one of the furnaces in service when that furnace must undergo a decoking operation.

In a more particularly preferred manner, step a) is carried out in three cracking furnaces. In a most particularly preferred manner, step a) is carried out in three different cracking furnaces, the mixtures of cracking products derived from each of them being gathered together before step b). With a more particular advantage, a fourth cracking furnace is available to replace one of the three furnaces in service when that furnace must undergo a decoking operation.

It is therefore particularly advantageous to carry out step a) in three different cracking furnaces, the mixtures of cracking products derived from each of them being gathered together before step b) and to make a fourth cracking furnace available to replace one of the three furnaces in service.

After this first cracking step a), said mixture of cracking products is subjected to a series of treatment steps making it possible to obtain a mixture of products containing ethylene and other constituents.

Step b) is advantageously composed of the following steps: thermal recovery of the heat of the cracked gases, optionally organic quenching (optionally including heat recovery across a network of exchangers with intermediate liquids), aqueous quenching, compressing and drying of the gases, and also removing most of the carbon dioxide and most of the sulphur compounds that are present or added (for example, by means of an alkaline wash), optionally hydrogenating undesirable derivatives such as, for example, acetylene and optionally eliminating some of the hydrogen and/or methane, for example via a PSA (pressure swing adsorption) process or via a membrane process.

Advantageously, in the process according to the invention, the mixture of products containing ethylene and other constituents derived from step b) comprises hydrogen, methane, compounds comprising from 2 to 7 carbon atoms, carbon monoxide, nitrogen and oxygen. Hydrogen, methane and compounds comprising from 2 to 7 carbon atoms other than acetylene are preferably present in an amount of at least 200 ppm by volume relative to the total volume of said mixture of products. Carbon monoxide, nitrogen, oxygen and acetylene may be present in an amount of less than 200 ppm by volume or in an amount of at least 200 ppm by volume relative to the total volume of said mixture of products. Compounds containing more than 7 carbon atoms, carbon dioxide, hydrogen sulphide and the other sulphur compounds and also water may also be present in the abovementioned mixture of products in an amount of less than 200 ppm by volume relative to the total volume of said mixture of products.

The compression and drying of the gases may be advantageously performed under particular conditions so that the passage of the compounds comprising at least 6 carbon atoms is minimized. The cooling fluid which may be used is advantageously at a temperature lower than the temperature of the water from an atmospheric cooling tower. The cooling fluid is preferably at a temperature of at least $-5°$ C., more preferably of at least $0°$ C. The cooling fluid is most preferably iced water.

After step b) defined above, the mixture of products containing ethylene and other constituents is subjected to step c) which is a first separation step S1 that consists of separating said mixture of products inside a main column C1, into a fraction enriched with the compounds that are lighter than ethylene containing some of the ethylene (fraction A) and into a fraction F1.

Prior to its introduction into column C1, the mixture of products derived from step b) may be subjected to a thermal conditioning step. The term "thermal conditioning step" is understood to mean a series of heat exchanges optimizing the use of energy, for example the gradual cooling of the mixture of products in a set of exchangers first cooled with untreated water, then with iced water, and then with increasingly cold liquids plus cross exchangers recovering the sensible heat of the streams produced.

Said mixture of products may be introduced into the column C1 during step S1 as a single fraction or as several subfractions. It is preferably introduced as several subfractions.

Column C1 is advantageously a column comprising a stripping section and/or a rectifying section. If both sections are present, the rectifying section preferably surmounts the stripping section.

Column C1 is advantageously chosen from distillation columns comprising the two aforementioned sections and the columns that only include one of the two sections. Preferably, column C1 is a distillation column.

The distillation column may be chosen from plate distillation columns, distillation columns with random packing, distillation columns with structured packing and distillation columns combining two or more of the abovementioned internals.

Step S1 is therefore preferably a distillation step.

Column C1 is advantageously equipped with associated accessories such as, for example, at least one reboiler and at least one condenser.

Fraction A enriched with the compounds that are lighter than ethylene containing some of the ethylene, advantageously exits from the top of column C1 whereas fraction F1, advantageously enriched with the least volatile compounds, advantageously exits from the bottom of column C1.

The abovementioned step S1 is advantageously carried out at a pressure of at least 5, preferably at least 10 and particularly preferably at least 12 bar absolute. Step S1 is advantageously carried out at a pressure of at most 40, preferably at most 38 and particularly preferably at most 36 bar absolute.

The temperature at which step S1 is carried out is advantageously at least 0, preferably at least 5 and particularly preferably at least $10°$ C. at the bottom of column C1. It is advantageously at most 80, preferably at most 60 and particularly preferably at most $40°$ C. at the bottom of column C1.

The temperature at which step S1 is carried out is advantageously at least $-70$, preferably at least $-60$ and particularly preferably at least $-55°$ C. at the top of column C1. It is advantageously at most 0, preferably at most $-15$ and particularly preferably at most $-25°$ C. at the top of column C1.

Fraction A is enriched with compounds that are lighter than ethylene. These compounds are generally methane, nitrogen, oxygen, hydrogen and carbon monoxide. Advantageously, fraction A contains at least 70%, preferably at least 80% and particularly preferably at least 85% by weight of compounds that are lighter than ethylene contained in the mixture of products subjected to step c). Advantageously, fraction A contains at most 99.99%, preferably at most 99.95% and particularly preferably at most 99.9% by weight of compounds that are lighter than ethylene contained in the mixture of products subjected to step c).

Advantageously, fraction A contains at least 10%, preferably at least 20% and particularly preferably at least 25% by volume of methane relative to the total volume of fraction A. Advantageously, fraction A contains at most 80%, preferably at most 75% and particularly preferably at most 70% by volume of methane relative to the total volume of fraction A.

Advantageously, fraction A contains at least 90%, preferably at least 93% and particularly preferably at least 95% of the methane contained in the mixture of products subjected to step c).

Advantageously, fraction A contains at least 2%, preferably at least 4% and particularly preferably at least 3% by volume of hydrogen relative to the total volume of fraction A. Advantageously, fraction A contains at most 60%, preferably at most 50% and particularly preferably at most 45% by volume of hydrogen relative to the total volume of fraction A.

Advantageously, fraction A contains at least 95%, preferably at least 97% and particularly preferably at least 99% of the hydrogen contained in the mixture of products subjected to step c).

Advantageously, fraction A contains at least 5%, preferably at least 10% and particularly preferably at least 15% of the acetylene contained in the mixture of products subjected to step c). Advantageously, fraction A contains at most 95%, preferably at most 90% and particularly preferably at most 85% of the acetylene contained in the mixture of products subjected to step c).

When an acetylene hydrogenation takes place during step b), fraction A is characterized by an acetylene content that is advantageously less than or equal to 0.01%, preferably less than or equal to 0.005% and particularly preferably less than or equal to 0.001% by volume relative to the total volume of fraction A.

Advantageously, fraction A contains at most 20%, preferably at most 12% and particularly preferably at most 8% of the ethane contained in the mixture of products subjected to step c).

Fraction A is characterized by a content of compounds containing at least 3 carbon atoms that is advantageously less than or equal to 0.01%, preferably less than or equal to 0.005% and particularly preferably less than or equal to 0.001% by volume relative to the total volume of fraction A.

The fraction A is characterized by a content of sulphur compounds that is advantageously less than or equal to 0.005%, preferably less than or equal to 0.002% and particularly preferably less than or equal to 0.001% by volume relative to the total volume of fraction A.

Advantageously, fraction F1 contains at most 30%, preferably at most 20% and particularly preferably at most 15% of compounds that are lighter than ethylene contained in the mixture of products subjected to step c).

Fraction F1 is advantageously characterized by a methane content of less than or equal to 10%, preferably of less than or equal to 5% and particularly preferably of less than or equal to 2% by volume relative to the total volume of fraction F1.

Fraction F1 is advantageously characterized by a hydrogen content of less than or equal to 5%, preferably of less than or equal to 2% and particularly preferably of less than or equal to 1% by volume relative to the total volume of fraction F1.

Fraction F1 is additionally characterized by an acetylene content that is advantageously less than or equal to 2%, preferably less than or equal to 1.5% and particularly preferably less than or equal to 1% by volume relative to the total volume of fraction F1.

Advantageously, fraction F1 contains at least 85%, preferably at least 90% and particularly preferably at least 95%, by volume relative to the total volume of fraction F1, of compounds containing at least 2 carbon atoms.

Advantageously, fraction F1 contains at most 70%, preferably at most 60% and particularly preferably at most 50% by volume relative to the total volume of fraction F1, of compounds having more than 2 carbon atoms.

After step c) defined above, fraction F1 is subjected to a second separation step S2 which consists of separating fraction F1 inside a column C2 into a fraction F2 and into a heavy fraction (fraction C).

Prior to its introduction into column C2, the mixture of products derived from step c) may be subjected to a thermal and/or chemical conditioning step, such as, for example, an acetylene hydrogenation. The term "thermal conditioning step" is understood to mean a series of heat exchanges optimizing the use of energy, for example the gradual cooling of the mixture of products in a set of exchangers first cooled with untreated water, then with iced water, and then with increasingly cold liquids plus cross exchangers recovering the sensible heat of the streams produced.

Said mixture of products may be introduced into column C2 during step S2 as a single fraction or as several subfractions. It is preferably introduced as several subfractions.

Column C2 is advantageously a column comprising a stripping section and/or a rectifying section. If both sections are present, the rectifying section preferably surmounts the stripping section.

Column C2 is advantageously chosen from distillation columns comprising the two aforementioned sections and the columns that only include one of the two sections. Preferably, column C2 is a distillation column.

The distillation column may be chosen from plate distillation columns, distillation columns with random packing, distillation columns with structured packing and distillation columns combining two or more of the abovementioned internals.

Step S2 is therefore preferably a distillation step.

Column C2 is advantageously equipped with associated accessories such as, for example, at least one reboiler and at least one condenser.

Fraction F2, advantageously enriched with the most volatile compounds, advantageously exits from the top of column C2 whereas the heavy fraction C, advantageously enriched with the least volatile compounds, advantageously exits from the bottom of column C2.

The abovementioned step S2 is advantageously carried out at a pressure of at least 5, preferably at least 8 and particularly preferably at least 10 bar absolute. Step S2 is advantageously carried out at a pressure of at most 40, preferably at most 37 and particularly preferably at most 35 bar absolute.

The temperature at which step S2 is carried out is advantageously at least 0, preferably at least 10 and particularly preferably at least 15° C. at the bottom of column C2. It is advantageously at most 90, preferably at most 86 and particularly preferably at most 83° C. at the bottom of column C2.

The temperature at which step S2 is carried out is advantageously at least −65, preferably at least −55 and particularly preferably at least −50° C. at the top of column C2. It is advantageously at most 5, preferably at most 0 and particularly preferably at most −2° C. at the top of column C2.

Fraction C advantageously contains a small amount of ethane and compounds comprising at least 3 carbon atoms. Advantageously, the compounds constituting fraction C stem from the mixture of products containing ethylene and other constituents derived from step b). Fraction C also advantageously contains the compounds containing at least 3 carbon atoms generated by secondary reactions during steps c) and d). Among the compounds comprising at least 3 carbon atoms, mention may be made of propane, propene, butanes and their unsaturated derivatives and also all the saturated or unsaturated heavier compounds.

The expression "a small amount of ethane" is understood to mean that fraction C contains at most 5%, preferably at most 3% and particularly preferably at most 2% of the ethane contained in the mixture of products subjected to step d).

Fraction C advantageously contains at least 90%, preferably at least 93% and particularly preferably at least 95% by weight of compounds comprising at least 3 carbon atoms relative to the total weight of fraction C.

Fraction C advantageously contains at most 1%, preferably at most 0.8% and particularly preferably at most 0.5% by weight of ethylene relative to the total weight of fraction C.

After being obtained during step d), fraction C is advantageously subjected to at least one hydrogenation step. Preferably, it is subjected to one or two successive hydrogenation steps. One step of separating, for example by distillation, into two different fractions that respectively contain compounds comprising less than 5 carbon atoms for one of the fractions, and compounds comprising at least 5 carbon atoms for the other one, may be carried out before, between or after the hydrogenation steps. When such a separation is carried out before a hydrogenation step, the hydrogenation advantageously takes place on the compounds comprising less than 5 carbon atoms.

According to a first case, fraction C is advantageously subjected to two hydrogenation steps, preferably followed by a step of separating, for example by distillation, into two different fractions that respectively contain compounds comprising less than 5 carbon atoms for one of the fractions, and compounds comprising at least 5 carbon atoms for the other one. This separation step is particularly preferably followed by recycling the compounds comprising less than 5 carbon atoms to the cracking step. The compounds comprising at least 5 carbon atoms are themselves, in a particularly preferred manner, burnt to provide energy or upgraded to any form whatsoever.

According to a second case, a separation step consisting of separating fraction C, for example by distillation, into two different fractions respectively containing compounds comprising less than 5 carbon atoms for one of the fractions, and compounds comprising at least 5 carbon atoms for the other one, is advantageously carried out. The resultant fraction containing the compounds comprising less than 5 carbon atoms is then preferably subjected to two hydrogenation steps before recycling to the cracking step. As for the compounds comprising at least 5 carbon atoms, they are, in a particularly preferred manner, burnt to provide energy or upgraded to any form whatsoever.

According to a third case, fraction C is advantageously subjected to one hydrogenation step, preferably followed by a step of separating, for example by distillation, into two different fractions that respectively contain compounds comprising less than 5 carbon atoms for one of the fractions, and compounds comprising at least 5 carbon atoms for the other one. This separation step is particularly preferably followed by recycling the compounds comprising less than 5 carbon atoms to the cracking step. The compounds comprising at least 5 carbon atoms are themselves, in a particularly preferred manner, burnt to provide energy or upgraded to any form whatsoever.

According to a fourth case, a separation step consisting of separating fraction C, for example by distillation, into two different fractions respectively containing compounds comprising less than 5 carbon atoms for one of the fractions, and compounds comprising at least 5 carbon atoms for the other one, is advantageously carried out. The resultant fraction containing the compounds comprising less than 5 carbon atoms is then preferably subjected to one hydrogenation steps before recycling to the cracking step. As for the compounds comprising at least 5 carbon atoms, they are, in a particularly preferred manner, burnt to provide energy or upgraded to any form whatsoever.

The abovementioned hydrogenation step may be performed by means of any known hydrogenation catalyst such as, for example, catalysts based on palladium, platinum, rhodium, ruthenium or iridium deposited on a support such as alumina, silica, silica/alumina, carbon, calcium carbonate or barium sulphate, but also catalysts based on nickel and those based on the cobalt-molybdenum complex. Preferably, the hydrogenation step is performed by means of a catalyst based on palladium or platinum deposited on alumina or carbon, on a catalyst based on nickel or on a catalyst based on the cobalt-molybdenum complex. In a particularly preferred manner, it is performed by means of a catalyst based on nickel.

The temperature at which the hydrogenation step is performed is advantageously at least 5° C., preferably at least 20° C., in a particularly preferred manner at least 50° C. It is advantageously at most 150° C., preferably at most 100° C. As for the pressure, it is advantageously greater than or equal to 1 bar, preferably greater than or equal to 3 bar. It is advantageously less than or equal to 40 bar, preferably less than or equal to 35 bar, in a particularly preferred manner less than or equal to 30 bar, in a most particularly preferred manner less than or equal to 25 bar and most advantageously less than or equal to 20 bar.

Preferably, the hydrogenation step is performed using quantities of hydrogen such that it is complete, that is to say preferably at at least 99%. The excess hydrogen not consumed may be separated from the hydrogenated fraction or may be optionally conveyed to the first pyrolysis step with it when this is the case.

The hydrogenation step is advantageously performed in the gas phase or in the liquid phase. Preferably, it is performed in the liquid phase.

It can be advantageous to absorb the calories of the reaction by means of at least one external exchanger or by partial evaporation of the liquid. The calories of the reaction are preferably absorbed by means of at least one external exchanger. The external exchanger may advantageously be integrated into the reactor or implemented on an external loop. When integrated into the reactor, the external exchanger may be integrated into one zone combining the heat exchange and the reaction (multi-tubular fix bed) or in successive heat exchanging and reaction zones. The external exchanger is preferably implemented on an external loop. The external loop may advantageously be gas or liquid, preferably liquid.

The hydrogenation may advantageously be performed in a slurry type reactor, a fixed bed type reactor with one or more beds, preferably with one bed, or the combination thereof. Preferably, the hydrogenation is performed in a fixed bed reactor, more preferably in a fixed bed reactor with only one bed. The fixed bed reactor may be characterized by a continuous gas phase or by a continuous liquid phase, preferably by a continuous gas phase, more preferably by a continuous gas phase with a flow of the liquid from top to bottom (trickle bed). The hydrogenation reaction is most preferably performed in a trickle bed with one bed equipped with an external exchanger implemented on an external loop.

Fraction F2 advantageously contains at most 0.01%, preferably at most 0.005% and particularly preferably at most 0.001% by volume of compounds comprising least 3 carbon atoms relative to the total volume of fraction F2.

Fraction F2 is additionally characterized by an acetylene content that is advantageously less than or equal to 2%, preferably less than or equal to 1.5% and particularly preferably less than or equal to 1% by volume relative to the total volume of fraction F2.

Fraction F2 is characterized by a content of sulphur compounds that is advantageously less than or equal to 0.005%, preferably less than or equal to 0.002% and particularly preferably less than or equal to 0.001% by volume relative to the total volume of fraction F2.

Fraction F2 is advantageously characterized by an ethylene content that is greater than or equal to 50%, preferably greater than or equal to 60% and particularly preferably greater than or equal to 65% by volume relative to the total volume of fraction F2.

After step d) defined above, fraction F2 is subjected to a third separation step S3 which consists of separating fraction F2 inside a column C3 into a fraction enriched with ethylene (fraction B) and into a fraction F3 mainly composed of ethane.

Prior to its introduction into column C3, the mixture of products derived from step d) may be subjected to a thermal and/or chemical conditioning step, such as, for example, an acetylene hydrogenation. The term "thermal conditioning step" is understood to mean a series of heat exchanges optimizing the use of energy, for example the gradual cooling of the mixture of products in a set of exchangers first cooled with untreated water, then with iced water, and then with increasingly cold liquids plus cross exchangers recovering the sensible heat of the streams produced.

Said mixture of products may be introduced into column C3 during step S3 as a single fraction or as several subfractions. It is preferably introduced as several subfractions.

Column C3 is advantageously a column comprising a stripping section and/or a rectifying section. If both sections are present, the rectifying section preferably surmounts the stripping section.

Column C3 is advantageously chosen from distillation columns comprising the two aforementioned sections and the columns that only include one of the two sections. Preferably, column C3 is a distillation column.

The distillation column may be chosen from plate distillation columns, distillation columns with random packing, distillation columns with structured packing and distillation columns combining two or more of the abovementioned internals.

Step S3 is therefore preferably a distillation step.

Fraction B, enriched with ethylene, advantageously exits from the top of the column whereas fraction F3, mainly composed of ethane, advantageously exits from the bottom of the column.

The abovementioned step S3 is advantageously carried out at a pressure of at least 5, preferably at least 6 and particularly preferably at least 7 bar absolute. Step S3 is advantageously carried out at a pressure of at most 30, preferably at most 25 and particularly preferably at most 22 bar absolute.

The temperature at which step S3 is carried out is advantageously at least −50, preferably at least −45 and particularly preferably at least −40° C. at the bottom of column C3. It is advantageously at most 10, preferably at most 0 and particularly preferably at most −5° C. at the bottom of column C3.

The temperature at which step S3 is carried out is advantageously at least −70, preferably at least −65 and particularly preferably at least −60° C. at the top of column C3. It is advantageously at most −15, preferably at most −20 and particularly preferably at most −25° C. at the top of column C3.

Fraction B is advantageously characterized by a hydrogen content of less than or equal to 2%, preferably of less than or equal to 0.5% and particularly preferably of less than or equal to 0.1% by volume relative to the total volume of fraction B.

Fraction B is characterized by a content of compounds containing at least 3 carbon atoms that is advantageously less than or equal to 0.01%, preferably less than or equal to 0.005% and particularly preferably less than or equal to 0.001% by volume relative to the total volume of fraction B.

Fraction B is characterized by a content of sulphur compounds that is less than or equal to 0.005%, preferably less than or equal to 0.002% and particularly preferably less than or equal to 0.001% by volume relative to the total volume of fraction B.

Fraction B is additionally characterized by an acetylene content that is advantageously less than or equal to 2%, preferably less than or equal to 1.5% and particularly preferably less than or equal to 1% by volume relative to the total volume of fraction B.

Fraction F3 is mainly composed of ethane. The term "mainly composed" is understood to mean that it comprises at least 90% by volume of ethane relative to the total volume of fraction F3. It preferably comprises at least 95%, particularly preferably at least 97% and more particularly preferably at least 98% by volume of ethane relative to the total volume of fraction F3.

Fraction F3 is additionally characterized advantageously by an ethylene content that is less than or equal to 5%, preferably less than or equal to 3% and particularly preferably less than or equal to 1.5% by volume relative to the total volume of fraction F3.

Fraction F3 may be used for any purpose. Preferably, it is conveyed to step a). Fraction F3 may be conveyed to step a) as a starting material or as a fuel. In a particularly preferred manner, it is conveyed to step a) as a starting material.

Preferably, the separation steps S1, S2 and S3 of the process according to the invention are distillation steps, carried out, in a particularly preferred manner, in distillation columns.

The separation steps S1, S2 and S3 of the process according to the invention are advantageously thermally integrated. The thermal integration is preferably performed either directly, or via one or more refrigeration cycles with temperature levels which are more or less cold, preferably two refrigeration cycles with one at low temperature and the other at medium temperature, or via the combination thereof, more preferably via the combination thereof.

The refrigeration cycles are advantageously based on the compounds containing two carbon atoms, the compounds containing three carbon atoms or their mixtures. Among the compounds containing two carbon atoms, ethylene, ethane and mixtures thereof may be cited. Ethylene is preferred. Among the compounds containing three carbon atoms, propylene, propane and the mixtures thereof may be cited. Propylene is preferred.

The low temperature cycle and the medium temperature cycle are preferably interconnected, that means that the hot source of the low temperature cycle is a cold source of the medium temperature cycle while the hot source of the medium temperature cycle is water from an atmospheric cooling tower. The low temperature cycle preferably uses compounds with 2 carbon atoms and more preferably contains at least 95 mol % of ethylene. The medium temperature cycle preferably uses compounds with 3 carbon atoms and more preferably contains at least 95 mol % of propane or at least 95 mol % of propylene. More preferably, the medium temperature cycle contains at least 95 mol % of propylene.

After the steps defined above, fraction A is conveyed to a chlorination reactor and fraction B to an oxychlorination reactor, reactors in which most of the ethylene present in fractions A and B is converted into 1,2-dichloroethane.

According to the process according to the invention, fraction A is conveyed to a chlorination reactor and fraction B to an oxychlorination reactor, preferably after expansion with recovery of energy.

According to the process of the invention, the amounts defined below for characterizing fraction B and fraction A are those before their respective entry into the oxychlorination and chlorination reactors.

Fraction B advantageously contains from 40% to 99.65% by volume of ethylene relative to the total volume of fraction B. Fraction B advantageously contains at least 40%, preferably at least 50% and particularly preferably at least 60% by volume of ethylene relative to the total volume of fraction B. Fraction B advantageously contains at most 99.8%, preferably at most 99.7% and particularly preferably at most 99.65% by volume of ethylene relative to the total volume of fraction B.

Fraction A advantageously contains a volume content of ethylene such that it represents from 10% to 95% of the volume content of ethylene of fraction B. Fraction A advantageously contains a volume content of ethylene such that it is less than or equal to 98%, preferably less than or equal to 96% and particularly preferably less than or equal to 95% of the volume content of ethylene of fraction B. Fraction A advantageously contains a volume content of ethylene such that it is at least 5%, preferably at least 8% and particularly preferably at least 10% of the volume content of ethylene of fraction B.

According to a first variant of the process according to the invention, considering that the process for the manufacture of DCE is advantageously balanced (that is to say that the process for manufacturing by chlorination and oxychlorination of ethylene and pyrolysis of the 1,2-dichloroethane (DCE) formed makes it possible to generate the amount of HCl necessary for the process), the weight fraction of the ethylene throughput in each of fractions A and B is advantageously between 45 and 55% of the total amount of ethylene produced (fraction A+fraction B). Preferably, the weight fraction of the ethylene throughput in fraction A is around 55% and the weight fraction of the ethylene throughput in fraction B is around 45% of the total amount produced. In a particularly preferred manner, the weight fraction of the ethylene throughput in fraction A is around 52.5% and the weight fraction of the ethylene throughput in fraction B is around 47.5% of the total amount produced.

According to a second variant of the process according to the invention, considering that the process for the manufacture of DCE is advantageously unbalanced (that is to say, for example, that an external source of HCl makes it possible to provide part of the supply of HCl for the oxychlorination or that a fraction of the DCE produced is not subjected to pyrolysis), the weight fraction of the ethylene throughput in each of fractions A and B is advantageously between 20 and 80% of the total amount of ethylene produced (fraction A+fraction B). Preferably, the weight fraction of the ethylene throughput in fraction A is between 25 and 75% of the total amount of ethylene produced (fraction A+fraction B).

According to a first embodiment of the second variant of the process according to the invention, considering that the process for the manufacture of DCE is advantageously unbalanced by an external source of HCl, the mole fraction of the ethylene throughput in fraction A is advantageously between 45 and 55%, preferably between 50 and 54% and particularly preferably around 52.5% of the difference between the total molar amount of ethylene contained in the mixture of products subjected to step b) and the molar amount of HCl from the external source.

According to a second embodiment of the second variant of the process according to the invention, considering that the process for the manufacture of DCE is advantageously unbalanced by co-production of DCE (some of the DCE is therefore not subjected to pyrolysis), the mole fraction of the ethylene throughput in fraction B is advantageously between 45 and 55%, preferably between 46 and 50% and particularly preferably around 47.5% of the difference between the total molar amount of ethylene contained in the mixture of products subjected to step b) and the molar amount of DCE co-produced.

The chlorination reaction is advantageously carried out in a liquid phase (preferably mainly DCE) containing a dissolved catalyst such as $FeCl_3$ or another Lewis acid. It is possible to advantageously combine this catalyst with cocatalysts such as alkali metal chlorides. A pair which has given good results is the complex of $FeCl_3$ with LiCl (lithium tetrachloroferrate—as described in Patent Application NL 6901398).

The amounts of $FeCl_3$ advantageously used are around 1 to 30 g of $FeCl_3$ per kg of liquid stock. The molar ratio of $FeCl_3$ to LiCl is advantageously of the order of 0.5 to 2.

In addition, the chlorination process is preferably performed in a chlorinated organic liquid medium. More preferably, this chlorinated organic liquid medium, also called liquid stock, mainly consists of DCE.

The chlorination process according to the invention is advantageously performed at temperatures between 30 and 150° C. Good results were obtained regardless of the pressure both at a temperature below the boiling point (chlorination under subcooled conditions) and at the boiling point itself (chlorination at boiling point).

When the chlorination process according to the invention is a chlorination process under subcooled conditions, it gave good results by operating at a temperature which was advantageously greater than or equal to 50° C. and preferably greater than or equal to 60° C., but advantageously less than or equal to 80° C. and preferably less than or equal to 70° C., and with a pressure in the gaseous phase advantageously greater than or equal to 1 and preferably greater than or equal to 1.1 bar absolute, but advantageously less than or equal to 20, preferably less than or equal to 10 and particularly preferably less than or equal to 6 bar absolute.

A process for chlorination at boiling point may be preferred to usefully recover the heat of reaction. In this case, the reaction advantageously takes place at a temperature greater than or equal to 60° C., preferably greater than or equal to 70° C. and particularly preferably greater than or equal to 85° C., but advantageously less than or equal to 150° C. and preferably less than or equal to 135° C., and with a pressure in the gaseous phase advantageously greater than or equal to 0.2, preferably greater than or equal to 0.5, particularly preferably greater than or equal to 1.1 and more particularly preferably greater than or equal to 1.3 bar absolute, but advantageously less than or equal to 10 and preferably less than or equal to 6 bar absolute.

The chlorination process may also be a hybrid loop-cooled process for chlorination at boiling point. The expression "hybrid loop-cooled process for chlorination at boiling point" is understood to mean a process in which cooling of the reaction medium is carried out, for example, by means of an exchanger immersed in the reaction medium or by a loop circulating in an exchanger, while producing in the gaseous phase at least the amount of DCE formed. Advantageously, the reaction temperature and pressure are adjusted for the DCE produced to leave in the gaseous phase and for the remainder of the heat from the reaction medium to be removed by means of the exchange surface area.

Fraction A containing the ethylene and also the chlorine (itself pure or diluted) may be introduced, together or separately, into the reaction medium by any known device. A separate introduction of fraction A may be advantageous in order to increase its partial pressure and facilitate its dissolution which often constitutes a limiting step of the process.

The chlorine is added in a sufficient amount to convert most of the ethylene and without requiring the addition of an excess of unconverted chlorine. The chlorine/ethylene ratio used is preferably between 1.2 and 0.8 and particularly preferably between 1.05 and 0.95 mol/mol.

The chlorinated products obtained contain mainly DCE and also small amounts of by-products such as 1,1,2-trichloroethane or small amounts of ethane or methane chlorination products. The separation of the DCE obtained from the stream of products derived from the chlorination reactor is carried out according to known modes and in general makes it possible to exploit the heat of the chlorination reaction.

The unconverted products (methane, carbon monoxide, nitrogen, oxygen and hydrogen) are then advantageously subjected to an easier separation than what would have been necessary to separate pure ethylene starting from the initial mixture.

The oxychlorination reaction is advantageously performed in the presence of a catalyst comprising active elements including copper deposited on an inert support. The inert support is advantageously chosen from alumina, silica gels, mixed oxides, clays and other supports of natural origin. Alumina constitutes a preferred inert support.

Catalysts comprising active elements which are advantageously at least two in number, one of which is copper, are preferred. Among the active elements other than copper, mention may be made of alkali metals, alkaline-earth metals, rare-earth metals and metals from the group consisting of ruthenium, rhodium, palladium, osmium, iridium, platinum and gold. The catalysts containing the following active elements are particularly advantageous: copper/magnesium/potassium, copper/magnesium/sodium; copper/magnesium/lithium, copper/magnesium/caesium, copper/magnesium/sodium/lithium, copper/magnesium/potassium/lithium and copper/magnesium/caesium/lithium, copper/magnesium/sodium/potassium, copper/magnesium/sodium/caesium and copper/magnesium/potassium/caesium. The catalysts described in Patent Applications EP-A 255 156, EP-A 494 474, EP-A-657 212 and EP-A 657 213, incorporated by reference, are most particularly preferred.

The copper content, calculated in metal form, is advantageously between 30 and 90 g/kg, preferably between 40 and 80 g/kg and particularly preferably between 50 and 70 g/kg of catalyst.

The magnesium content, calculated in metal form, is advantageously between 10 and 30 g/kg, preferably between 12 and 25 g/kg and particularly preferably between 15 and 20 g/kg of catalyst.

The alkali metal content, calculated in metal form, is advantageously between 0.1 and 30 g/kg, preferably between 0.5 and 20 g/kg and particularly preferably between 1 and 15 g/kg of catalyst.

The Cu:Mg:alkali metal(s) atomic ratios are advantageously 1:0.1-2:0.05-2, preferably 1:0.2-1.5:0.1-1.5 and particularly preferably 1:0.5-1:0.15-1.

Catalysts having a specific surface area, measured according to the BET method with nitrogen that is advantageously between 25 $m^2/g$ and 300 $m^2/g$, preferably between 50 and 200 $m^2$g and particularly preferably between 75 and 175 $m^2/g$, are particularly advantageous.

The catalyst may be used in a fixed bed or in a fluidized bed. This second option is preferred. The oxychlorination process is operated under the range of the conditions usually recommended for this reaction. The temperature is advantageously between 150 and 300° C., preferably between 200 and 275° C. and most preferably from 215 to 255° C. The pressure is advantageously above atmospheric pressure. Values of between 2 and 10 bar absolute gave good results. The range between 4 and 7 bar absolute is preferred. This pressure may be usefully adjusted in order to attain an optimum residence time in the reactor and to maintain a constant rate of passage for various operating speeds. The usual residence times range from 1 to 60 s and preferably from 10 to 40 s.

The source of oxygen for this oxychlorination may be air, pure oxygen or a mixture thereof, preferably pure oxygen. The latter solution, which allows easy recycling of the unconverted reactants, is preferred.

The reactants may be introduced into the bed by any known device. It is generally advantageous to introduce the oxygen separately from the other reactants for safety reasons. These safety reasons also require the gaseous mixture leaving the reactor or recycled thereto to be kept outside the limits of inflammability at the pressures and temperatures in question. It is preferable to maintain a so-called rich mixture, that is to say containing too little oxygen relative to the fuel to ignite. In this regard, the abundant presence (>2 vol %, preferably >5 vol %) of hydrogen would constitute a disadvantage given the wide range of inflammability of this compound.

The hydrogen chloride/oxygen ratio used is advantageously between 3 and 6 mol/mol. The ethylene/hydrogen chloride ratio is advantageously between 0.4 and 0.6 mol/mol.

The chlorinated products obtained contain mainly DCE and also small amounts of by-products such as 1,1,2-trichloroethane. The separation of the DCE obtained from the stream of products derived from the oxychlorination reactor is carried out according to known modes. The heat of the oxychlorination reaction is generally recovered in vapour form which can be used for the separations or for any other purpose.

The unconverted products such as methane and ethane are then subjected to an easier separation than that which would have been necessary to separate pure ethylene starting from the initial mixture.

The DCE obtained by chlorination or by oxychlorination of ethylene may then be converted into VC.

The invention therefore also relates to a process for the manufacture of VC. To this effect, the invention relates to a process for the manufacture of VC according to which:

a) a hydrocarbon source is subjected to a first cracking step, namely a pyrolysis step carried out in at least one cracking furnace, thus producing a mixture of cracking products;

b) said mixture of cracking products is subjected to a series of treatment steps making it possible to obtain a mixture of products containing ethylene and other constituents;

c) said mixture of products containing ethylene is subjected to a first separation step S1 which consists of separating said mixture of products inside a column C1, into a fraction enriched with the compounds that are lighter than ethylene containing some of the ethylene (fraction A) and into a fraction F1;

d) fraction F1 is subjected to a second separation step S2 which consists of separating fraction F1 inside a column C2 into a fraction F2 and into a heavy fraction (fraction C);

e) fraction F2 is subjected to a third separation step S3 which consists of separating fraction F2 inside a column C3 into a fraction enriched with ethylene (fraction B) and into a fraction F3 mainly composed of ethane;

f) fraction A is conveyed to a chlorination reactor and fraction B is conveyed to an oxychlorination reactor, reactors in which most of the ethylene present in fractions A and B is converted to 1,2-dichloroethane;

g) the 1,2-dichloroethane obtained is separated from the streams of products derived from the chlorination and oxychlorination reactors; and h) the 1,2-dichloroethane obtained is subjected to a pyrolysis, thus producing the VC.

The particular conditions and preferences defined for the process for the manufacture of DCE according to the invention apply to the process for the manufacture of VC according to the invention.

The conditions under which the pyrolysis may be carried out are known to a person skilled in the art. This pyrolysis is advantageously achieved by a reaction in the gas phase in a tube furnace. The usual pyrolysis temperatures extend between 400 and 600° C. with a preference for the range between 480° C. and 540° C. The residence time is advantageously between 1 and 60 seconds with a preference for the range from 5 to 25 seconds. The conversion rate of the DCE is advantageously limited to 45 to 75% to limit the formation of by-products and fouling of the furnace pipes. The following steps make it possible, using any known device, to collect the purified VC and the hydrogen chloride to be upgraded preferably to the oxychlorination. Following purification, the unconverted DCE is advantageously conveyed to the pyrolysis furnace.

In addition, the invention also relates to a process for the manufacture of PVC. To this effect, the invention relates to a process for the manufacture of PVC according to which:

a) a hydrocarbon source is subjected to a first cracking step, namely a pyrolysis step carried out in at least one cracking furnace, thus producing a mixture of cracking products;

b) said mixture of cracking products is subjected to a series of treatment steps making it possible to obtain a mixture of products containing ethylene and other constituents;

c) said mixture of products containing ethylene is subjected to a first separation step S1 which consists of separating said mixture of products inside a column C1, into a fraction enriched with the compounds that are lighter than ethylene containing some of the ethylene (fraction A) and into a fraction F1;

d) fraction F1 is subjected to a second separation step S2 which consists of separating fraction F1 inside a column C2 into a fraction F2 and into a heavy fraction (fraction C);

e) fraction F2 is subjected to a third separation step S3 which consists of separating fraction F2 inside a column C3 into a fraction enriched with ethylene (fraction B) and into a fraction F3 mainly composed of ethane;

f) fraction A is conveyed to a chlorination reactor and fraction B is conveyed to an oxychlorination reactor, reactors in which most of the ethylene present in fractions A and B is converted to 1,2-dichloroethane;

g) the 1,2-dichloroethane obtained is separated from the streams of products derived from the chlorination and oxychlorination reactors;

h) the 1,2-dichloroethane obtained is subjected to a pyrolysis, thus producing VC; and i) the VC is polymerized to produce PVC.

The particular conditions and preferences defined for the process for the manufacture of DCE and the process for the manufacture of VC according to the invention apply to the process for the manufacture of PVC according to the invention.

The process for the manufacture of PVC may be a bulk, solution or aqueous dispersion polymerization process, preferably it is an aqueous dispersion polymerization process.

The expression "aqueous dispersion polymerization" is understood to mean radical polymerization in aqueous suspension and also radical polymerization in aqueous emulsion and polymerization in aqueous microsuspension.

The expression "radical polymerization in aqueous suspension" is understood to mean any radical polymerization process performed in aqueous medium in the presence of dispersants and oil-soluble radical initiators.

The expression "radical polymerization in aqueous emulsion" is understood to mean any radical polymerization process performed in aqueous medium in the presence of emulsifiers and water-soluble radical initiators.

The expression "polymerization in aqueous microsuspension", also called polymerization in homogenized aqueous dispersion, is understood to mean any radical polymerization process in which oil-soluble initiators are used and an emulsion of monomer droplets is prepared by virtue of a powerful mechanical stirring and the presence of emulsifiers.

The process for the manufacture of DCE according to the invention has the advantage of using two different ethylene fractions that are well-suited to the chlorination reaction and to the oxychlorination reaction respectively. In particular, the process according to the invention has the advantage of using an ethylene fraction that is slightly contaminated with hydrogen for the oxychlorination reaction and this being at a cost that is not very high.

Another advantage of the process according to the invention is that it makes it possible to have, on the same industrial site, a completely integrated process ranging from the hydrocarbon source to the polymer obtained starting from the monomer manufactured.

An additional advantage of the process according to the invention is that it would make it possible, by a modification of the conditions for separating the fractions as defined below, to deal with situations where it is advantageous to develop an external source of hydrogen chloride, stemming from another manufacture such as, for example, a unit for manufacturing isocyanates. Conversely, it is possible to encounter the situation of an advantageous market for hydrogen chloride that results in a decrease on the part of the oxychlorination relative to the chlorination.

The process according to the invention is additionally advantageous because it makes it possible to separate the compounds comprising at least 3 carbon atoms via fraction C, compounds generally responsible for a certain inhibition during the pyrolysis of the DCE. This inhibition is due to the formation of derivatives such as 1,2-dichloropropane and monochloropropenes. These derivatives are difficult to completely separate from DCE. Their aptitude for forming stable allyl radicals explains their powerful inhibitory effect on the pyrolysis of DCE which is carried out by a radical route. The formation of these by-products containing three carbon atoms or heavier by-products would furthermore constitute an unnecessary consumption of reactants in the oxychlorination and in the chlorination, or would generate costs for destroying them. In addition, these heavy compounds contribute to the soiling of the columns and evaporators.

In relation to a process for the manufacture of DCE starting from a similar hydrocarbon source which would provide two separation steps instead of three, the process according to the invention that comprises an additional separation step, is characterized by a better separation of the compounds that are lighter than ethylene in the first separation step and by a better heat integration. It enables a better separation of ethane which may be upgraded and has the advantage of allowing lower reflux rates during each separation step. The fact that the process according to the invention makes it possible to separate the compounds that are heavier than ethylene into a fraction F3 mainly composed of ethane also has the advantage of increasing the boiling point of fraction C when it is subjected to hydrogenation.

The process for the manufacture of DCE according to the invention will now be illustrated with reference to the drawing accompanying the present description. This drawing consists of the appended FIG. 1, schematically representing an embodiment of the process for the manufacture of DCE according to the invention.

The mixture of products 1 containing ethylene and other constituents resulting from the cracking of a hydrocarbon source chosen from the group composed of propane, butane and propane/butane mixtures is introduced into column 2, which is a distillation column equipped with a bottom reboiler and an overhead condenser, where it is separated into 2 different fractions, namely fraction 3 at the top of column 2 and fraction 4 at the bottom of column 2.

Fraction 3, enriched with the compounds that are lighter than ethylene, in particular methane, hydrogen, nitrogen, oxygen and carbon monoxide, is conveyed to the ethylene chlorination unit.

Fraction 4 is then conveyed to a distillation column 5 equipped with a bottom reboiler and an overhead condenser.

After passing into column 5, fraction 4 is separated into fraction 6 exiting from the top of column 5 and into fraction 7 exiting from the bottom of column 5.

Fraction 6 is then conveyed to a distillation column 8 equipped with a bottom reboiler and an overhead condenser.

After passing into column 8, the fraction 6 is separated into fraction 9 exiting from the top of column 8 and into fraction 10 that is mainly composed of ethane.

Fraction 9, being characterized by a very low hydrogen content, is conveyed to the ethylene oxychlorination unit.

The invention claimed is:

1. A process for the manufacture of 1,2-dichloroethane starting with a hydrocarbon source, comprising:
   a) subjecting the hydrocarbon source to a first cracking step carried out in at least one cracking furnace, thus producing a mixture of cracking products;
   b) subjecting said mixture of cracking products to a series of treatment steps making it possible to obtain a mixture of products containing ethylene and other constituents;
   c) subjecting said mixture of products containing ethylene to a first separation step S1 which consists of separating said mixture of products inside a column C1, into a fraction enriched with the compounds that are lighter than ethylene containing some of the ethylene (fraction A) and into a fraction F1;
   d) subjecting said fraction F1 to a second separation step S2 which consists of separating fraction F1 inside a column C2 into a fraction F2 and into a heavy fraction (fraction C);
   e) subjecting said fraction F2 to a third separation step S3 which consists of separating fraction F2 inside a column C3 into a fraction enriched with ethylene (fraction B) and into a fraction F3 mainly composed of ethane;
   f) conveying said fraction A to a chlorination reactor and said fraction B to an oxychlorination reactor, wherein in said chlorination and oxychlorination reactors, most of the ethylene present in fractions A and B is converted to 1,2-dichloroethane; and
   g) separating the 1,2-dichloroethane obtained from step f) from the streams of products derived from the chlorination and oxychlorination reactors.

2. The process according to claim 1, wherein the hydrocarbon source is selected from the group consisting of naphtha, gas oil, natural gas liquid, ethane, propane, butane, isobutane, and mixtures thereof.

3. The process according to claim 1, wherein the hydrocarbon source is selected from the group consisting of ethane, propane, butane, and propane/butane mixtures.

4. The process according to claim 1, wherein step a) is carried out in three different cracking furnaces, the mixtures of cracking products derived from each of them being gathered together before step b), and wherein a fourth cracking furnace is made available to replace one of the three furnaces in service.

5. The process according to claim 1, wherein the mixture of products containing ethylene and other constituents derived from step b) comprises hydrogen, methane, compounds comprising from 2 to 7 carbon atoms, carbon monoxide, nitrogen, and oxygen.

6. A process for the manufacture of 1,2-dichloroethane starting with a hydrocarbon source, comprising:
   a) subjecting the hydrocarbon source to a first cracking step carried out in at least one cracking furnace, thus producing a mixture of cracking products;
   b) subjecting said mixture of cracking products to a series of treatment steps making it possible to obtain a mixture of products containing ethylene and other constituents;
   c) subjecting said mixture of products containing ethylene to a first separation step S1 which consists of separating said mixture of products inside a column C1, into a fraction enriched with the compounds that are lighter than ethylene containing some of the ethylene (fraction A) and into a fraction F1;
   d) subjecting said fraction F1 to a second separation step S2 which consists of separating fraction F1 inside a column C2 into a fraction F2 and into a heavy fraction (fraction C);
   e) subjecting said fraction F2 to a third separation step S3 which consists of separating fraction F2 inside a column C3 into a fraction enriched with ethylene (fraction B) and into a fraction F3 mainly composed of ethane;
   f) conveying said fraction A to a chlorination reactor and said fraction B to an oxychlorination reactor, wherein in said chlorination and oxychlorination reactors, most of the ethylene present in fractions A and B is converted to 1,2-dichloroethane; and
   g) separating the 1,2-dichloroethane obtained from step f) from the streams of products derived from the chlorination and oxychlorination reactors,
   wherein the separation steps S1, S2 and S3 are distillation steps.

7. The process according to claim 1, wherein said fraction B contains from 40% to 99.65% by volume of ethylene relative to the total volume of fraction B.

8. The process according to claim 1, wherein said fraction A contains a volume content of ethylene such that it represents from 10% to 95% of the volume content of ethylene of fraction B.

9. A process for the manufacture of vinyl chloride, comprising:

a) subjecting a hydrocarbon source to a first cracking step carried out in at least one cracking furnace, thus producing a mixture of cracking products;
b) subjecting said mixture of cracking products to a series of treatment steps making it possible to obtain a mixture of products containing ethylene and other constituents;
c) subjecting said mixture of products containing ethylene to a first separation step S1 which consists of separating said mixture of products inside a column C1, into a fraction enriched with the compounds that are lighter than ethylene containing some of the ethylene (fraction A) and into a fraction F1;
d) subjecting said fraction F1 to a second separation step S2 which consists of separating fraction F1 inside a column C2 into a fraction F2 and into a heavy fraction (fraction C);
e) subjecting said fraction F2 to a third separation step S3 which consists of separating fraction F2 inside a column C3 into a fraction enriched with ethylene (fraction B) and into a fraction F3 mainly composed of ethane;
f) conveying said fraction A to a chlorination reactor and said fraction B to an oxychlorination reactor, wherein in said chlorination and oxychlorination reactors, most of the ethylene present in fractions A and B is converted to 1,2-dichloroethane;
g) separating the 1,2-dichloroethane obtained from step f) from the streams of products derived from the chlorination and oxychlorination reactors; and
h) subjecting the 1,2-dichloroethane obtained to a pyrolysis, thus producing vinyl chloride.

10. A process for the manufacture of polyvinyl chloride, comprising:
a) subjecting a hydrocarbon source to a first cracking step carried out in at least one cracking furnace, thus producing a mixture of cracking products;
b) subjecting said mixture of cracking products to a series of treatment steps making it possible to obtain a mixture of products containing ethylene and other constituents;
c) subjecting said mixture of products containing ethylene to a first separation step S1 which consists of separating said mixture of products inside a column C1 , into a fraction enriched with the compounds that are lighter than ethylene containing some of the ethylene (fraction A) and into a fraction F1;
d) subjecting said fraction F1 to a second separation step S2 which consists of separating fraction F1 inside a column C2 into a fraction F2 and into a heavy fraction (fraction C);
e) subjecting said fraction F2 to a third separation step S3 which consists of separating fraction F2 inside a column C3 into a fraction enriched with ethylene (fraction B) and into a fraction F3 mainly composed of ethane;
f) conveying said fraction A to a chlorination reactor and said fraction B to an oxychlorination reactor, wherein in said chlorination and oxychlorination reactors, most of the ethylene present in fractions A and B is converted to 1,2-dichloroethane;
g) separating the 1,2-dichloroethane obtained from step f) from the streams of products derived from the chlorination and oxychlorination reactors;
h) subjecting the 1,2-dichloroethane obtained to a pyrolysis, thus producing vinyl chloride; and
i) polymerizing the vinyl chloride to produce polyvinyl chloride.

11. The process according to claim 1 wherein the first cracking step is a pyrolysis step.

12. The process according to claim 9 wherein the first cracking step is a pyrolysis step.

13. The process according to claim 10 wherein the first cracking step is a pyrolysis step.

14. The process according to claim 1 further comprising
h) subjecting the 1,2-dichloroethane obtained to a pyrolysis to produce vinyl chloride.

15. The process according to claim 1 further comprising
h) subjecting the 1,2-dichloroethane obtained to a pyrolysis to produce vinyl chloride, and
i) polymerizing the vinyl chloride to produce polyvinyl chloride.

16. The process according to claim 6, wherein the hydrocarbon source is selected from the group consisting of naphtha, gas oil, natural gas liquid, ethane, propane, butane, isobutane, and mixtures thereof.

17. The process according to claim 6, wherein said fraction B contains from 40% to 99.65% by volume of ethylene relative to the total volume of fraction B.

18. The process according to claim 6, wherein said fraction A contains a volume content of ethylene such that it represents from 10% to 95% of the volume content of ethylene of fraction B.

19. The process according to claim 6, further comprising
h) subjecting the 1,2-dichloroethane obtained to a pyrolysis to produce vinyl chloride.

20. The process according to claim 6, further comprising
h) subjecting the 1,2-dichloroethane obtained to a pyrolysis to produce vinyl chloride, and
i) polymerizing the vinyl chloride to produce polyvinyl chloride.

* * * * *